Figure 1:
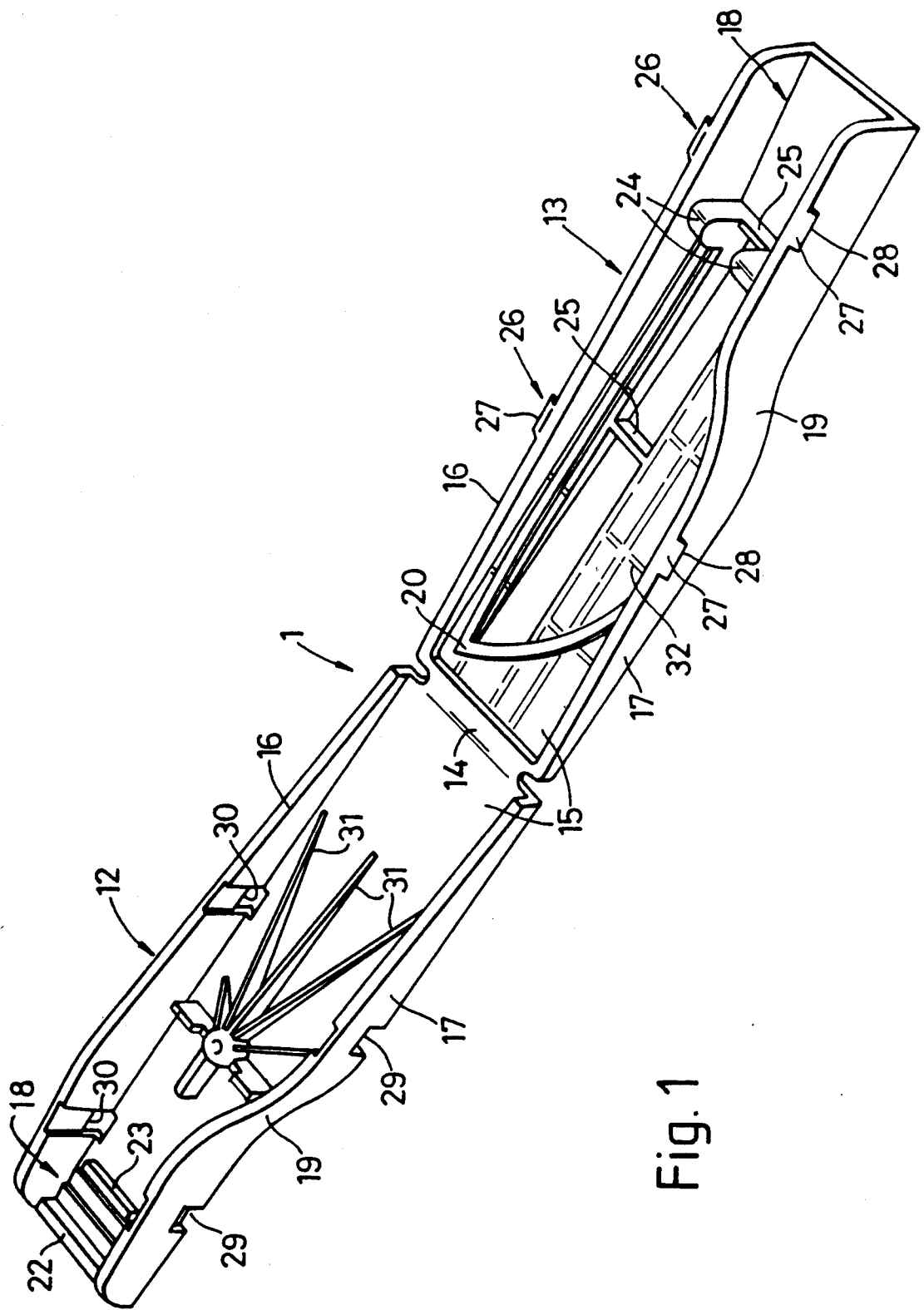

United States Patent [19]
Pemberton et al.

[11] Patent Number: 4,998,334
[45] Date of Patent: Mar. 12, 1991

[54] BLADE EXTRACTOR

[75] Inventors: John H. Pemberton; Stephen L. Dear, both of Harlow, England

[73] Assignee: Swann-Morton Limited, Sheffield, England

[21] Appl. No.: 477,038

[22] Filed: Feb. 7, 1990

[30] Foreign Application Priority Data

Feb. 15, 1989 [GB] United Kingdom ............... 8903391

[51] Int. Cl.$^5$ ............................................. B23P 19/04
[52] U.S. Cl. ....................................... 29/239; 206/359
[58] Field of Search ............... 206/352, 363, 216, 359, 206/355, 349; 30/339; 29/808, 235, 239, 270, 278

[56] References Cited

U.S. PATENT DOCUMENTS

| | | | |
|---|---|---|---|
| 4,730,376 | 3/1988 | Yamada | 206/355 |
| 4,746,016 | 5/1988 | Pollak et al. | 206/359 |
| 4,903,390 | 2/1990 | Vidal et al. | 29/278 |

*Primary Examiner*—Robert C. Watson
*Attorney, Agent, or Firm*—R. A. Giangiorgi

[57] ABSTRACT

A blade extractor (1) for a replaceable blade instrument or tool (3), which comprises upper and lower tabs (12, 13) of length slightly exceeding that of a blade (2) to be extracted, and of width slightly exceeding that of a blade (2) to be extracted with side skirts (16, 17) provided on one or both tabs (12, 13), abutment means (22) provided on one tab (12), and with the tabs (12, 13) being hinged together and being manually and progressively displaceable from a splayed-apart, open position to a closed position, in which closed position the tabs (12, 13) encapsulate the blade (2), and lie in substantially parallel planes, with opposite longitudinal edges of the tabs (12, 13) and hence the extractor (1) closed off by the side skirts (16, 17), and the abutment means (22) engages a portion (11) of the blade (2) so that, when the user manoeuvers the instrument or tool (3) with respect to the extractor (1) during the extraction process, the blade (2) is safely encapsulated within the extractor (1).

9 Claims, 4 Drawing Sheets

BLADE EXTRACTOR

This invention relates to a blade extractor for a replaceable blade of an instrument such as a surgeons scalpel, or of a tool such as a handicraft knife, a used or blunted blade being removed from the instrument or tool for replacement by a fresh blade. A scalpel blade for instance is conventionally provided with a longitudinally extending, two width slot, which is first a slide fit along a correspondingly shaped rib provided on a blade-receiving head of the scalpel and then finally snapped or pressed into a retaining position with an angled end of the blade abutting a correspondingly angled face of the scalpel head, while craft knife blades are retained by a variety of means including the scalpel type of snap-fit.

Although a used or blunted blade can be removed by handling between a thumb and finger this is not without risk, particularly if the blade involved is a contaminated scalpel blade, and consequently a known blade extractor, for surgical use, comprises a box like receptacle having internally a blade engaging means whereby an engaged blade may be pulled from the scalpel handle to fall automatically into the box interior, the latter being adapted to receive a plurality of blades, and when full the box itself is safely disposed of. One difficulty with this type of extractor is reliability of operation, in that blade extraction sometimes fails and repeated attempts must be made to effect extraction. Another problem area is that if the receptacle should become inverted, a blade(s) within the receptacle interior can present a handling hazard by becoming exposed or even falling out of the receptacle box, and contaminated surgical blades present an increasing health hazard to medical staff.

According to the present invention there is provided a blade extractor for a replaceable blade instrument or tool, which comprises upper and lower tabs of length slightly exceeding that of a blade to be extracted, and of width slightly exceeding that of a blade to be extracted with side skirts provided on one or both tabs, abutment means provided on one tab, and with the tabs being hinged together and being manually and progressively displaceable from a splayed-apart, open position to a closed position, in which closed position the tabs encapsulate the blade, and lie in substantially parallel planes, with opposite longitudinal edges of the tabs and hence the extractor closed off by the side skirts, and the abutment means engages a portion of the blade so that, when the user manoeuvers the instrument or tool with respect to the extractor during the extraction process, the blade is safely encapsulated within the extractor.

Thus, the extractor in accordance with the invention ensures safe blade extraction as it positively avoids the need for human finger/thumb contact with the blade during the extraction process, to remove any hazard to persons removing or handling the used and frequently contaminated scalpel or other blade.

Encapsulation may be temporary or permanent. In the former case encapsulation is effected only during the dangerous blade-extraction step, and after extraction the extractor may be opened and the blade allowed to fall from the extractor into a receptable or bin, e.g. adapted to accept a plurality of blades before safe disposal. In the latter case this extractor, in contrast to prior art proposals, is adapted to house but one blade permanently and safely, even removing any hazard of contact to persons in disposing of an extracted blade. In either case, latching means may be provided to latch the tabs together either temporarily or permanently.

Conveniently, the extractor is of synthetic plastics material, produced by injection moulding, and preferably the nature and/or wall thickness of the plastics material is such that the tabs are semi-flexible. The plastics material may be transparent, so that a user may readily see when a used blade has been captivated within the extractor, or alternatively if not transparent, then a window may be provided in one or both of the tabs. In detail, the two tabs may be integral, with a common interconnecting hinge formed by a transverse weakened or thinned portion of plastics material.

As is well known, to extract a scalpel blade the angled end of the blade must first be prised or flexed from its retaining position, and to achieve this, one tab may be provided with a transverse pressure bar and the other tab may be provided with an inwardly extending and preferably bifucated blade-flexing projection the pressure bar and tab being adapted to be brought by the user into contact with opposite sides of a portion of the blade adjacent the angled end, whereby during closing of the two tabs around a blade, the angled blade end is flexed away from the angled face of the scalpel head either automatically or after slight movement between the extractor and the scalpel, as a first step in releasing and prior to the second step, being the longitudinal slide of the blade along the rib of the head, as the extractor and scalpel are pulled apart to complete the extraction, which second step is conveniently effected by the other tab being provided with the abutment means which is adapted to make driven engagement with the angled end of the blade and hence trap and thereby retain the blade within the extractor, as the scalpel head is withdrawn from the extractor. The abutment may be constituted by a transverse rib or end wall of one tab, or may be generally "V"-shaped e.g. by being formed from two ribs upstanding from the inner surface of one tab.

In the case of a craft knife, if no suitable portion engageable by the abutment means is present, a portion can be provided by suitably cutting and/or notching the blade.

The latching means is conveniently located on the longitudinal sides of the tabs, and may conveniently comprise at least one pair of projections on one tab each adapted to engage a latching surface presented by the other tab. With one pair of projections and surfaces, these are preferably provided towards an end of their respective tabs remote from the hinge. With two pairs, these are spaced apart longitudinally of the tabs. It is also preferred for the projection to be flexible, so that latching is automatic upon closing of the extractor around a blade. Conveniently, each projection has an angled, lead-in face, and a latching face adapted to engage the latching surface of the other tab, which surface can simply be the external surface of that tab either on outer edge surface, or alternatively ends of the projections may pass through suitable apertures e.g. elongate slots.

Although the side skirts may be provided along the opposite lateral edges of one tab only e.g. the tab carrying the abutment means, preferably side skirts are provided along both tabs, with the tabs of differing widths, so that the skirts of one tab will just fit within the skirts of the other tab. With this arrangement, the projections may be provided on the outer edges of the skirts of one tab i.e. the tab having the bifurcated flexing projection, which is preferably the narrower tab, with receiving apertures provided at the junction of the skirts and wider tab.

Figure 2:
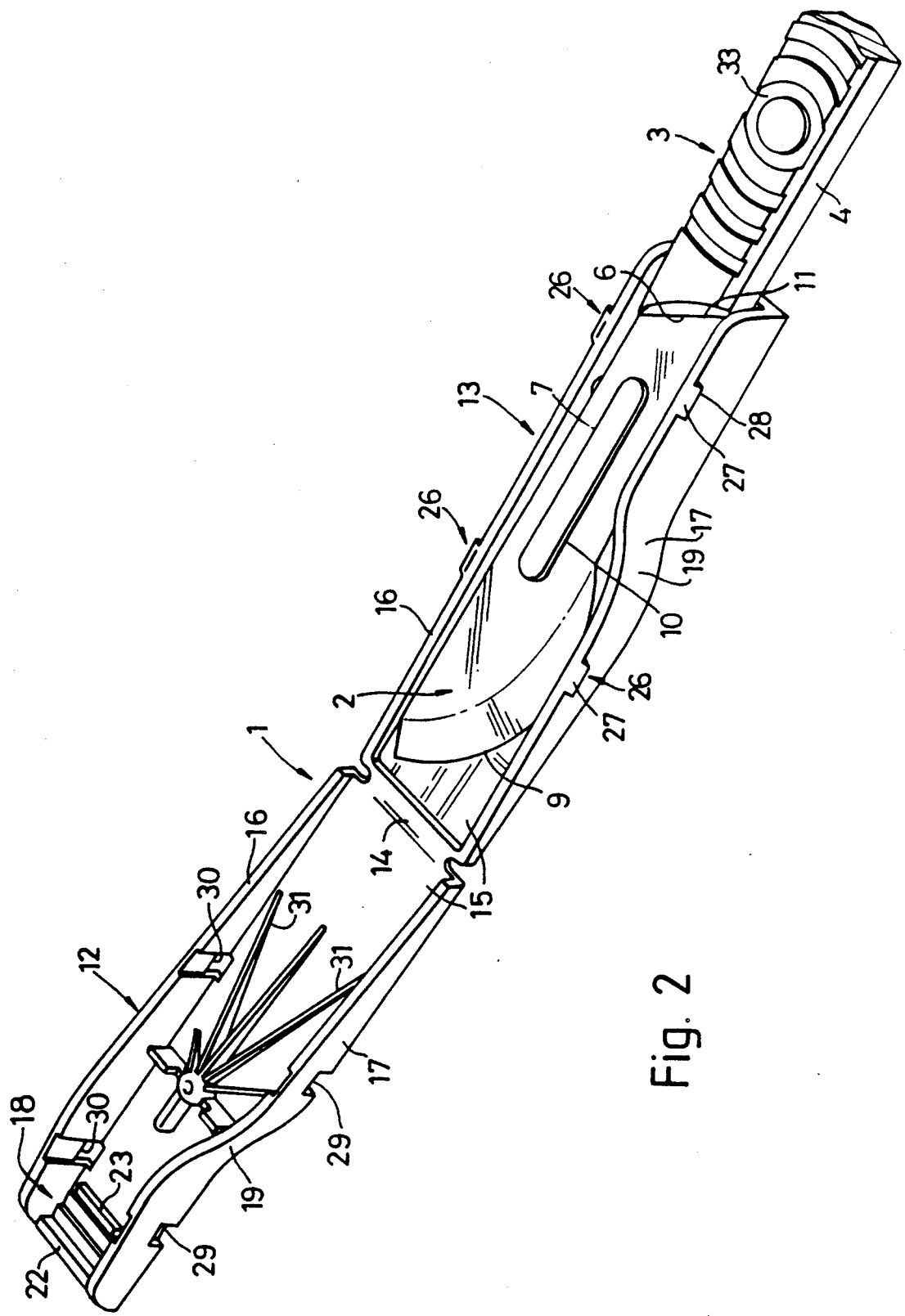
Figure 3:
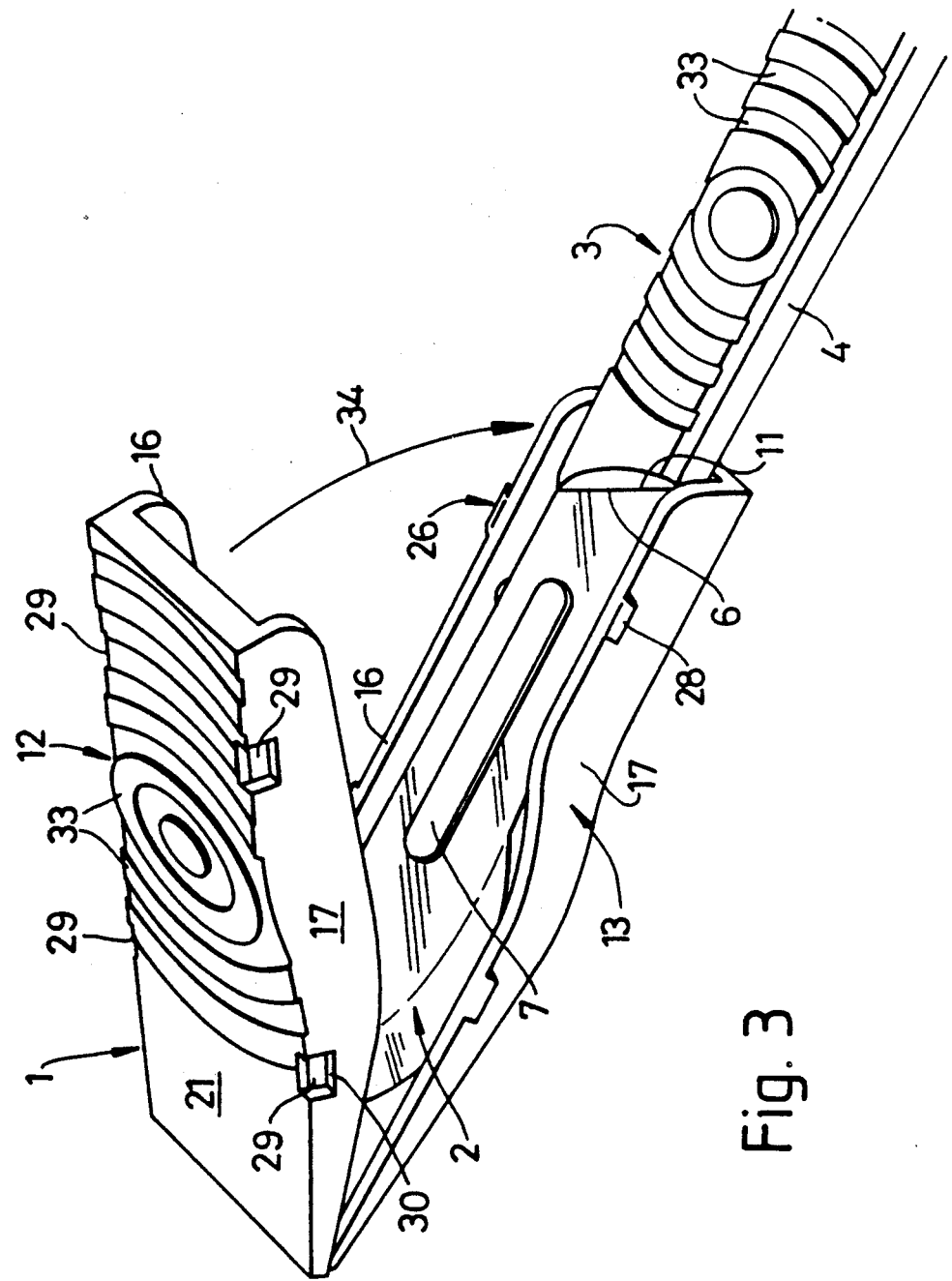
Figure 4:
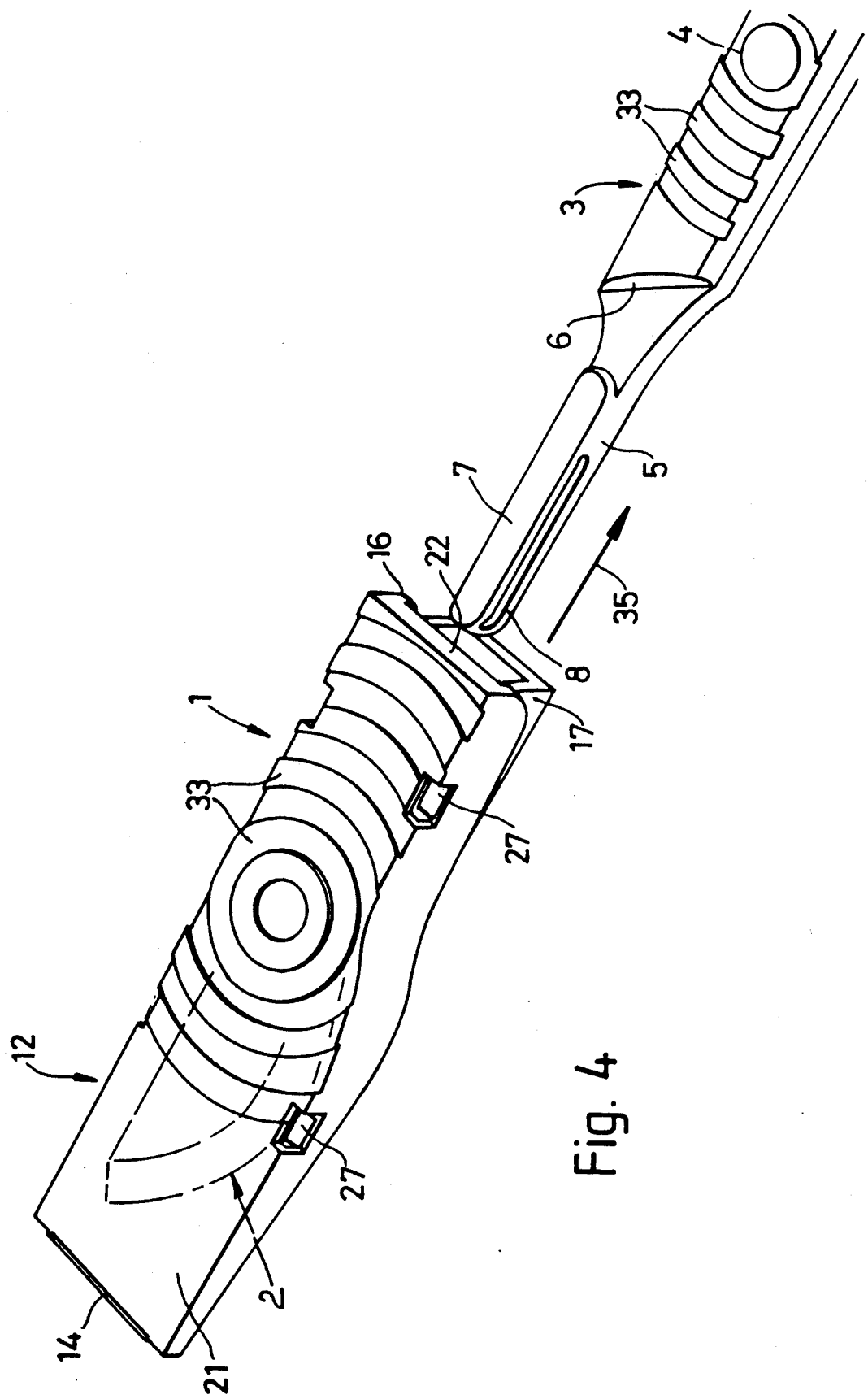

The invention will now be described in greater detail, by way of example, with reference to the accompanying drawings in which:

FIG. 1 is a perspective view of a blade extractor in accordance with the invention, in a first, open position; and FIGS. 2 to 4 show progressively the various stages of extraction of a scalpel blade.

In the drawings is illustrated a blade extractor 1 for extracting a replaceable scalpel blade 2 from a conventional scalpel 3 which comprises a handle 4 and an integral head 5. The latter has an angled abutment face 6 and an elongate rib 7 which is undercut at 8 except at its end adjacent the face 6. The blade 2 is likewise conventional being provided with a bowed, cutting edge 9, with a two-width slot 10, of length corresponding to that of the rib 7 and adapted to be fitted over the rib 7 and secondly with an angled end 11 into, or out of engagement with the abutment face 6.

The extractor 1, comprises basically upper and lower tabs 12, 13 of length and width slightly exceeding the corresponding dimensions of the blade 2.

The tabs 12 and 13 are produced in transparent, synthetic plastics material as a one-piece injection moulding with a common interconnecting hinge 14 formed by a transversely thinned portion of plastics material, of a nature and/or wall thickness such that the tabs are semi-flexible. Each tab 12, 13 is basically of channel section, comprising a web 15 formed integrally with upstanding side skirts 16, 17 along each longitudinal edge, the skirts diminishing in height towards the hinge 14. Remote from the hinge 14, the skirts are parallel over a throat portion 18, after which one skirt 17 is widened at 19 not only to accommodate the bowed cutting edge 9 of the blade 2 but also for improved thumb and finger grip by the user during the blade extraction process. Furthermore the web of the lower tab 13 has a raised perimeter 20, of profile corresponding to that of a blade 2 and adapted to constitute a blade-receiving bed, and an outer face 21 adapted to be gripped by the user. Also, the web 15 of the upper tab 12 is slightly wider than the web 15 of the lower tab 13, such that the skirts 16, 17 of the lower tab 13 will just fit within the skirts 16, 17 of the upper tab 12, when the extractor 1 is closed around a blade 2, as illustrated in FIG. 4.

At its end remote from the hinge 14, the upper tab 12 is provided with an integral, transversely extending abutment means in the form of an end wall 22 and spaced inwardly from the wall 22 and pressure bar 23, while the lower tab 13 is provided with a bifurcated projection 24, between which projection the scalpel head 5 is adapted to be accommodated, seating on two longitudinally spaced apart, transverse ribs 25.

The two tabs may be latched together in the closed position of the extractor by a latching means comprising, on the lower tab 13 two pairs of projections 26, spaced longitudinally along the tab, and formed integrally, on outer edges of the side skirts 16, 17. Each projection comprises an angled lead-in face 27 and a latching face 28. The upper tab 12 is provided with four correspondingly located elongate slots 29 at the junction between the skirts 16, 17 and their web 15, each slot 29 being engageable by a projection 26, and each slot exposing a latching surface 30 for engagement by a respective latching face 28.

Finally, on its inner face the web 14 of the upper tab 12 has an array of reinforcing ribs 31, while the lower tab 13 is provided with an array of longitudinal and transverse reinforcing ribs 32. Concentric rings 33 on the outer face 21 of the upper tab 12 and on the handle 4 are not only a trade mark of the Applicant, but also by their surface interruption improve the users grip on both components.

To effect blade extraction, an extractor 1 is opened to the splayed apart position illustrated in FIG. 1, and a blade 2 and scalpel head are placed in the lower tab 13, as illustrated in FIG. 2. The upper part 12 is then rotated about the hinge 14, a s indicated by arrow 34 until the position illustrated in FIG. 3 is attained whereupon not only do the projections 26 snap automatically into their latching positions, but the pressure bar 23 and projection 24 flex the end of the blade 2 adjacent its angled end 11 such that the end 11 is disengaged from the abutment face 6 upon slight movement between the blade extractor 1 and the scalpel 3. Thereafter, the blade extractor 1 and the scalpel can be pulled or drawn apart, as illustrated by the arrow 35 in FIG. 4 as the angled end 11 of the blade 2 abuts the end wall 22 of the upper tab 12, so that the end wall 22 pushes the blade along the rib 7 until, when clear of the rib 7 the scalpel head 5 is free to emerge from the extractor 1 without its blade 2. Because of the transparent nature of the plastics material of the extractor 1, the user can see a blade 2 successfully extracted and captivated within the extractor 1, the latching means illustrated being of a form intended for permanent encapsulation of a single blade.

What we claim is:

1. A blade extractor for extracting a blade from a replaceable blade instrument, said extractor comprising upper and lower tabs of length slightly exceeding that of said blade, and of width slightly exceeding that of said blade, side skirts provided on at least one of said tabs, abutment means provided on one of said tabs and said tabs being hinged together and being manually and progressively displaceable from a splayed-apart, open position to a closed position, in which closed position said tabs encapsulate said blade, and lie in substantially parallel planes, with opposite longitudinal edges of said tabs and hence the extractor closed off by said side skirts, and said abutment means engages a portion of said blade so that, when the user manoeuvers said instrument with respect to said extractor during said extraction process, said blade is safely encapsulated within said extractor.

2. A blade extractor as claimed in claim 1, wherein latching means are provided to latch said tabs together.

3. A blade extractor as claimed in claim 1, wherein said extractor is produced of transparent, semi-flexible synthetic plastics material, by injection moulding.

4. A blade extractor as claimed in claim 3, wherein said two tabs are integral, a common interconnecting hinge being formed between said tabs by a transverse weakened or thinned portion of plastics material.

5. A blade extractor as claimed in claim 1, wherein one of said tabs is provided with an inwardly extending, blade-flexing projection.

6. A blade extractor as claimed in claim 5, wherein a transverse pressure bar is also provided on the other of said tabs, which tab is provided with said abutment means.

7. A blade extractor as claimed in claim 2, wherein said latching means comprises at least one pair of projections on one of said tabs each adapted to engage a latching surface presented by said other tab.

8. A blade extractor as claimed in claim 7, wherein each said projection is flexible and has an angled, lead-in face, and also a latching face adapted automatically to engage said latching surface of said other tab when said extractor is moved to its closed position.

9. A blade extractor for extracting a blade from a replaceable blade instrument, said extractor comprising upper and lower tabs of length slightly exceeding that of said blade, and of width slightly exceeding that of said blade, and of width slightly exceeding that of said blade, side skirts provided along both said tabs, with said tabs being of differing widths, so that said side skirts of one said tab will just fit within said side skirts of the other said tab, abutment means provided on one of said tabs and said tabs being hinged together and being manually and progressively displaceable from a splayed-apart, open position to a closed position, in which closed position said tabs encapsulate said blade, and lie in substantially parallel planes, with opposite longitudinal edges of said tabs and hence the extractor closed off by said side skirts, and said abutment means engages a portion of said blade so that, when the user maneuvers said instrument with respect to said extractor during said extraction process, said blade is safely encapsulated within said extractor.

* * * * *